United States Patent
Rodgers et al.

(10) Patent No.: US 7,572,356 B2
(45) Date of Patent: Aug. 11, 2009

(54) ELECTROCHEMICAL-BASED SENSOR WITH A REDOX POLYMER AND REDOX ENZYME ENTRAPPED BY A DIALYSIS MEMBRANE

(75) Inventors: James Iain Rodgers, Lochardil (GB); Zuifang Liu, Milton of Leys (GB); Geoffrey Lillie, Inverness (GB)

(73) Assignee: Lifescan Scotland Limited, Inverness, Scotland (GB)

( * ) Notice: Subject to any disclaimer, the term of this patent is extended or adjusted under 35 U.S.C. 154(b) by 796 days.

(21) Appl. No.: 10/931,724

(22) Filed: Aug. 31, 2004

(65) Prior Publication Data
US 2006/0042944 A1 Mar. 2, 2006

(51) Int. Cl.
*G01N 27/327* (2006.01)
(52) U.S. Cl. .................. 204/403.05; 204/403.1
(58) Field of Classification Search .......... 204/224, 204/403.01–403.15; 205/777.5, 778, 792
See application file for complete search history.

(56) References Cited

U.S. PATENT DOCUMENTS

| | | | |
|---|---|---|---|
| 4,224,125 A | | 9/1980 | Nakamura et al. |
| 4,711,245 A | | 12/1987 | Higgins et al. |
| 5,089,112 A | | 2/1992 | Skotheim et al. |
| 5,262,035 A | | 11/1993 | Gregg et al. |
| 5,264,104 A | * | 11/1993 | Gregg et al. ............ 204/403.09 |
| 5,312,590 A | | 5/1994 | Gunasingham et al. |
| 6,284,478 B1 | | 9/2001 | Heller et al. |
| 6,420,036 B1 | * | 7/2002 | Varaprasad et al. ......... 428/432 |
| 6,485,703 B1 | * | 11/2002 | Cote et al. ................ 424/9.1 |
| 2002/0008038 A1 | * | 1/2002 | Heller et al. ............... 205/261 |
| 2004/0147673 A1 | * | 7/2004 | Calabro et al. ............ 525/54.1 |

FOREIGN PATENT DOCUMENTS

WO WO 01/21827 A 3/2001

OTHER PUBLICATIONS

"Amperometric Glucose Sensors Based on Ferrocene-containing B-polyethylenimine and immobilized Glucose Oxidase", C.L. Chuang, Y.J. Wang, H.L. Lan, Analytica Chimica Acta vol. 353 pp. 37-44 (May 14, 1997).*
ThermoScientifc TECH TIP #20, downloaded from www.piercenet.com/files/TR0020-Dialysis-overiw.pdf on Dec. 3, 2008.*
Rajagopalan et al, "Electrical communication between glucose oxidase and electrodes based on poly(vinylimidazole) complex of bis(2,2'-bipyridine)-N,N'-dichloroosmium", ACS Symposium Series (1994), 556 (Diagnostic Biosensor Polymers), 307-17.*

(Continued)

*Primary Examiner*—Alex Noguerola
(74) *Attorney, Agent, or Firm*—Mayumi Maeda (57) ABSTRACT

An electrochemical-based sensor includes an electrode with at least one electrode surface, a film disposed on the electrode surface, and a dialysis membrane disposed on the film. The film includes a redox enzyme and a hydrophilic redox polymer (i.e., a polymer with an attached redox mediator(s)). In addition, the dialysis membrane serves to entrap the redox polymer and redox enzyme in the vicinity of the electrode. Such entrapment is accomplished by employing a redox enzyme and a hydrophilic redox polymer of a sufficiently high molecular weight that they do not pass through the dialysis membrane.

4 Claims, 9 Drawing Sheets

OTHER PUBLICATIONS

Hale, Paul D., et al., "Amperometric Glucose Biosensors Based on Redox Polymer-Mediated Electron Transfer", Anal. Chem. 1991, 63, pp. 677-682.

Heller, Adam, Electrical Wiring of Redox Enzymes, Acc. Chem. Res. vol. 23, No. 5 1990, pp. 128-134.

Kuramoto, Noriyuki, et al., Property of thermo-sensitive and redox-active poly(N-cyclopropylacrylamide-co-vinylferrocene) and poly(N-isopropylacrylamide-co-vinylferrocene), Polymer, vol. 39 No. 3, pp. 669-675, 1998.

Saito, Takahiro, et al., "Characterization of poly(vinylferrocene-*co*-2-hydroxyethyl methacrylate) for use as electron mediator in enzymatic glucose sensor", Reactive & Functional Polymers 37 (1998) pp. 263-269.

* cited by examiner

ELECTROCHEMICAL-BASED SENSOR WITH A REDOX POLYMER AND REDOX ENZYME ENTRAPPED BY A DIALYSIS MEMBRANE

BACKGROUND OF INVENTION

1. Field of the Invention

The present invention relates, in general, to sensors and, in particular, to electrochemical-based sensors.

2. Description of the Related Art

The use of electrochemical-based sensors that employ a redox mediator and a redox enzyme in conjunction with an electrode(s) for the determination of an analyte in a liquid sample has become of heightened interest. Such electrochemical-based sensors are believed to be particularly suitable for continuous or semi-continuous monitoring of analytes (such as glucose) in bodily fluid samples (e.g., blood or interstitial fluid samples). For example, electrochemical-based glucose sensors employing a redox mediator, a redox enzyme and a working electrode can determine (i.e., measure) glucose concentration using relatively low potentials (e.g., less than 0.4 V vs SCE), thereby limiting any interfering responses, at the working electrode. For a further description of electrochemical-based sensors, see for example, U.S. Pat. Nos. 5,089,112 and 6,284,478, each of which is hereby fully incorporated by reference.

In typical electrochemical-based sensors, the redox mediator facilitates electron transfer between the redox enzyme(s) and an electrode(s) of the electrochemical-based sensor. In doing so, the redox enzyme cycles between oxidized and reduced states, driven by the presence of analyte, a redox mediator and a surface of the electrode. The net result of such cycling is that electrons are either accepted or donated at the surface of the electrode while the redox enzyme essentially maintains its original oxidation state and catalytic characteristics.

For the determination of an analyte in an aqueous liquid sample (e.g., a bodily fluid sample such as blood, urine or interstitial fluid), a degree of water solubility for both the redox enzyme and redox mediator can be beneficial in terms of enabling adequately rapid reaction kinetics. Therefore, conventional electrochemical-based sensors may incorporate a redox enzyme and a redox mediator that are solvated in an aqueous liquid sample.

For electrochemical-based sensors that require long term stability, such as continuous or semi-continuous electrochemical-based glucose sensors, it is essential that the redox mediator does not leach away from the vicinity of the electrode. In addition, if the redox mediator is a substance that is harmful to humans or other subjects, leaching of the redox mediator into a human's or other subject's body is undesirable and thus to be avoided.

Redox mediators have been attached to water-insoluble synthetic polymer chains, such as polysilozanes, in order to prevent leaching. Such chemical compositions, however, suffer from low flexibility, and thus reduced reaction kinetics in aqueous media, due to their hydrophobic nature. Moreover, redox mediators covalently attached to hydrophilic polymer backbones are not suitable for efficient and secure conventional attachment directly to an electrode(s) of an electrochemical-based sensor.

Still needed in the field, therefore, is an electrochemical-based sensor that employs a redox enzyme and redox mediator, yet does not suffer from inadvertent leaching of the redox enzyme and/or redox mediator from the vicinity of the electrochemical-based sensor's electrode. In addition, the redox mediator and redox enzyme of such an electrochemical-based sensor should exhibit adequately rapid reaction kinetics.

SUMMARY OF INVENTION

Electrochemical-based sensors according to embodiments of the present invention include a redox enzyme and a redox mediator, yet do not suffer from inadvertent leaching of the redox enzyme and/or redox mediator from the vicinity of an electrode of the electrochemical-based sensor. In addition, the redox mediator and redox enzyme of such embodiments exhibit adequately rapid reaction kinetics.

An electrochemical-based sensor according to an embodiment of the present invention includes an electrode with at least one electrode surface, a film disposed on the electrode surface, and a dialysis membrane disposed on the film. The film includes a redox enzyme and a hydrophilic redox polymer (i.e., a polymer with an attached redox mediator(s), for example, a covalently attached redox mediator). In addition, the dialysis membrane serves to entrap the redox polymer and redox enzyme in the vicinity of the electrode. Such entrapment can be accomplished by employing a redox enzyme and a hydrophilic redox polymer of a sufficiently high molecular weight that they do not pass through the dialysis membrane.

Since both the redox enzyme and hydrophilic redox polymer are entrapped in the vicinity of the electrode by the dialysis membrane, leaching is prevented and the electrochemical-based sensor can be employed for continuous or semi-continuous measurements over an extended period of time (e.g., for ten hours or longer). Furthermore, the hydrophilic nature of the redox polymer provides for adequately rapid reaction kinetics in the presence of an aqueous liquid sample.

BRIEF DESCRIPTION OF DRAWINGS

A better understanding of the features and advantages of the present invention will be obtained by reference to the following detailed description that sets forth illustrative embodiments, in which principles of the invention are utilized, and the accompanying drawings of which:

FIGS. 8A and 8B depict the magnitude of the glucose catalytic current as a function of time for an electrode coated with the redox polymer of FIG. 2 and glucose oxidase, both with and without a dialysis membrane. FIG. 8B highlights the first 10 minutes of the 100-minute measurement that is shown in FIG. 8A.

DETAILED DESCRIPTION OF THE INVENTION

To be consistent throughout the present specification and for clear understanding of the present invention, the following definitions are hereby provided for terms used therein:

The term "redox mediator" refers to any chemical moiety capable of undergoing a reduction (accepting of an electron(s)) or oxidation (donation of an electron(s)) with both an electrode surface and a redox enzyme.

The term "hydrophilic" refers to any chemical species or subgroup with a high affinity for water or aqueous solutions. Therefore, a hydrophilic compound will tend to be attracted to, dissolve in, or be absorbed in water or an aqueous solution.

The term "hydrophobic" refers to any chemical species or subgroup with a low affinity for water or aqueous solutions. Therefore, a hydrophobic compound tends to repel and not be absorbed in water or an aqueous solution.

The term "redox polymer" refers to a polymer that has been modified (derivatized) to include at least one redox mediator.

FIGS. 1A through 1D depict a portion of an electrochemical-based sensor 100 according to an exemplary embodiment of the present invention. Electrochemical-based sensor 100 includes a substrate 102, a reference electrode 104a with an electrode surface 106a, a working electrode 104b with an electrode surface 106b, a film 108 disposed on electrode surface 106a, and a dialysis membrane 110 disposed on film 108. Electrochemical-based sensor 100 also includes an insulation layer 112 and a reference ink layer 114. One skilled in the art will recognize that FIGS. 1A through 1D depict only a portion of a complete electrochemical-based sensor and that additional components of the electrochemical-based sensor (e.g., a housing, analysis/microprocessor module, and electrical communication circuits) have not been illustrated to avoid unduly complicating FIGS. 1A through 1D.

One skilled in the art will also recognize that reference ink layer 114, which constitutes an electrochemically active layer integrated with reference electrode 104a, sets the "zero potential" against which a measurement potential is applied at working electrode 104b. One skilled in the art will further recognize that although FIGS. 1A through 1D depict an electrochemical-based sensor with a two electrode format, other electrochemical-based sensor formats known in the field can be employed in embodiments of the present invention.

Substrate 102 can be formed, for example, from a sheet of polyetheylene terephthallate, polybutylene terephthallate sheet (commercially available from, for example, GE Plastic, United States), or from an oriented polystyrene film (commercially available from, for example, NSW GmBH, Germany).

Reference ink layer 114 can be formed, for example, from Ag/AgCl paste (commercially available from Gwent Electronic Materials, Pontypool Wales, UK) or any suitable electrochemical reference material including, but not limited to materials that include a metal that forms a partially soluble salt (e.g., silver, copper, titanium and lithium).

Insulation layer 112 can be formed, for example, from a dielectric screen printable ink paste (commercially available from, for example, Sericol Inks Ltd.). Reference electrode 104a and working electrode 104b can be formed of any suitable material known to one skilled in the art. For example, reference and working electrodes 104a and 104b can be formed from conductive ink, such as a carbon conductive ink.

Reference electrode 104a, working electrode 104b, insulation layer 112 and dialysis membrane 110 can have any suitable thickness. However, a typical thickness for each of these layers is in the range of from 1 micron to 100 microns.

Film 108 includes a redox enzyme and a hydrophilic redox polymer (not depicted in FIG. 1). The redox polymer and redox enzyme of film 108 are entrapped in the vicinity of working electrode 104b by dialysis membrane 110 and insulation layer 112.

The hydrophilic redox polymer and redox enzyme of film 108 are both of a sufficiently high molecular weight that they essentially do not pass through dialysis membrane 110 (as discussed further below). The hydrophilic redox polymer and redox enzyme can have any suitable molecular weight that provides for the hydrophilic redox polymer to be entrapped by a given dialysis membrane. Typically, such hydrophilic redox polymers have a molecular weight of greater than about 10 kg mol$^{-1}$ (10,000 Daltons) and such redox enzymes have a molecular weight of greater than 5,000 Daltons (5 kg mol$^{-1}$) and preferably greater than 80,000 Daltons (80 kg mol$^{-1}$). In this regard, it is noted that glucose oxidase (a redox enzyme) has a molecular weight of approximately 160,000 Daltons (160 kg mol$^{-1}$).

Dialysis membrane 110 is adapted such that only relatively low molecular weight compounds (e.g., glucose) can pass therethrough, while relatively high molecular weight compounds (e.g., the hydrophilic redox polymer and redox mediator of film 108) are retained in the vicinity of working electrode 104b. The dialysis membrane can also function as an analyte (e.g., glucose) diffusion control layer and interferent excluding layer.

Dialysis membrane 110 can be any suitable dialysis membrane known in the art, including a cast polymer dialysis membrane or a cross-linked polymer dialysis membrane. Non-limiting examples of suitable dialysis membranes include (i) a cast dialysis membrane formed from an acetone solution containing 2% (w/v) cellulose acetate (CA) and 0.7% (w/v) polyethylene glycol (PEG) and (ii) a cross-linked polymer dialysis membrane formed from a 2-isopropanol solution containing 5% (w/v) polyethyleneimine (PEI) and 0.7% (w/v) poly(propylene glycol) diglycidyl ether (PPGDGE).

Hydrophilic redox polymers suitable for use in film 108 can be formed by, for example, covalently attaching a redox mediator to a relatively high molecular weight polymer. The hydrophilic nature of such a hydrophilic redox polymer facilitates a favorable interaction between the redox mediator of the hydrophilic redox polymer and the redox enzyme such that adequately rapid reaction kinetics are obtained.

The redox enzyme of film 108 can be any suitable redox enzyme known to one skilled in the art. Exemplary, but non-limiting examples include glucose oxidase, latate oxidase, bilirubin oxidase, sarcosine oxidase, choline oxidase, cholesterol oxidase, and xanthine oxidase, glucose dehydrogenase, alcohol dehydrogenase, peroxidase (e.g., horseradish peroxidase) and catalase.

It is a benefit of electrochemical-based sensors according to embodiments of the present invention that components thereof can be readily prepared and handled in solution during manufacturing. Therefore, the manufacturing of such electrochemical-based sensors can be achieved using, for example, conventional printing and coating techniques.

Figure 1A:
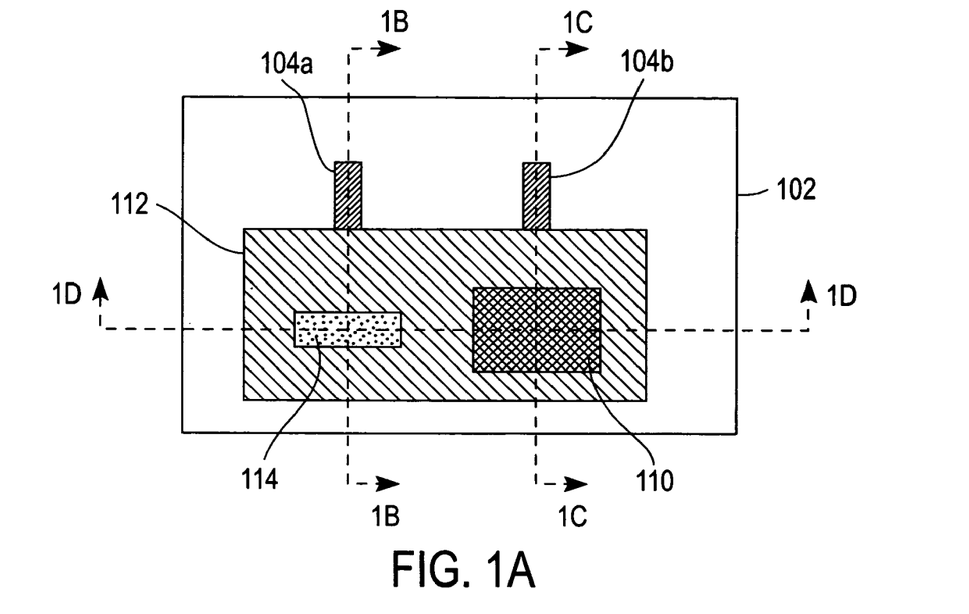
FIG. 1A is a simplified top view depiction of a portion of an electrochemical-based sensor according to an exemplary embodiment of the present invention.
Figure 1B:
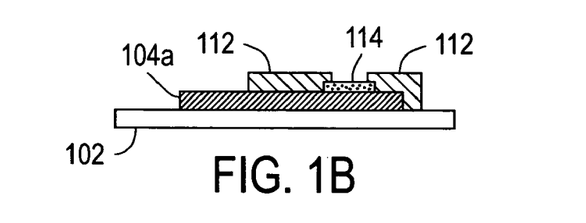
FIG. 1B is a simplified cross-sectional depiction of the electrochemical-based sensor of FIG. 1A taken along line 1B-1B.
Figure 1C:
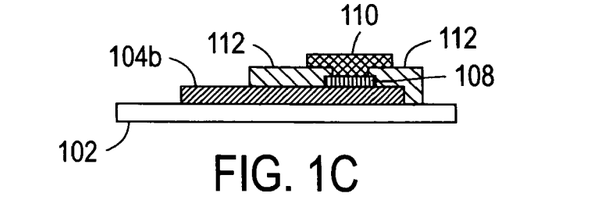
FIG. 1C is a simplified cross-sectional depiction of the electrochemical-based sensor of FIG. 1A taken along line 1C-1C.
Figure 1D:
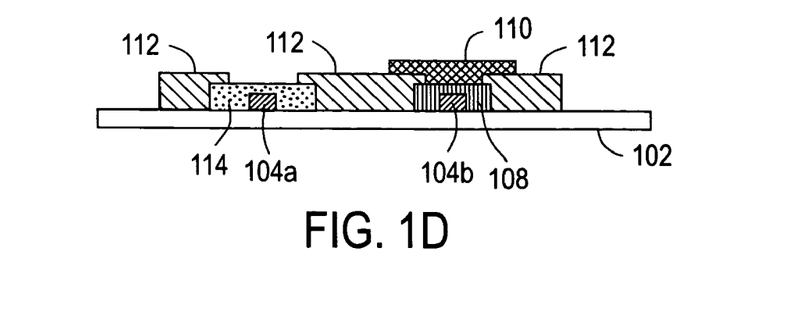
FIG. 1D is a simplified cross-sectional depiction of the electrochemical-based sensor of FIG. 1A taken along line 1D-1D.
Figure 2:
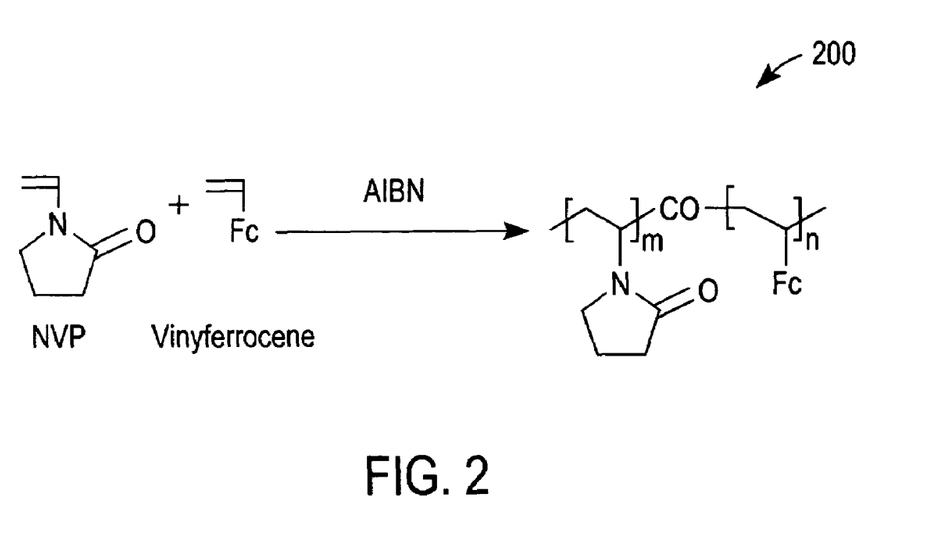
FIG. 2 is a simplified depiction of the co-polymerizing of N-vinylpyrrolidinone (NVP) and vinyl ferrocene (VFc) to form a redox polymer for use in electrochemical-based sensors according to exemplary embodiments of the present invention.

FIG. 2 is a schematic representation depicting a process for forming a redox polymer 200 suitable for use in electrochemical-based sensors according to exemplary embodiments of the present invention. As depicted in FIG. 2, redox polymer 200 can be formed by free radical co-polymerization of the hydrophilic monomer N-vinylpyrrolidinone (NVP) with the redox mediator vinyl ferrocene (VFc) initiated by 2,2'-azobisisobutyronitrile (AIBN). Alternative hydrophilic monomers known to those skilled in the art, such as acrylamide monomer, hydroxyethyl methacrylate nonomer and polyethylene glycol (PEG) macro-monomer, can be substituted for NVP.

The mole ratio of NVP:VFc is represented in FIG. 2 as m:n, can be, for example, in the range of from about 100:1 to about 100:5. It should be noted that if the proportion of VFc is greater than about 5%, the resulting redox polymer may become insoluble in some aqueous liquid samples. Moreover, if the proportion of VFc is less than about 1%, the redox conductivity of redox polymer 200 may become too low to support the electron exchange rates needed for determining glucose. It should also be noted that the hydrophilic character of NVP imparts a relatively high degree of hydrophilicity to redox polymer 200.

Redox polymers suitable for use in electrochemical-based sensors according to embodiments of the present invention can include any suitable redox mediator including, but not limited to, osmium complexes, quinone, ferricyanide, methylene blue, 2,6-dichloroindophenol, thionine, gallocyanine, indophenol and combinations thereof. Furthermore, the redox polymers can be formed, for example, from any suitable hydrophilic monomer including, but not limited to, hydrophilic monomers with an acrylate or a vinyl polymerizable functional group. Examples of other hydrophilic monomers suitable for use include hydroxyethyl methacrylate, N-isopropylacrylamide, glycerol methacrylate and acrylamide. For different mediators and hydrophilic monomers, changes should be accordingly made to the process shown in FIG. 2.

Figure 3:
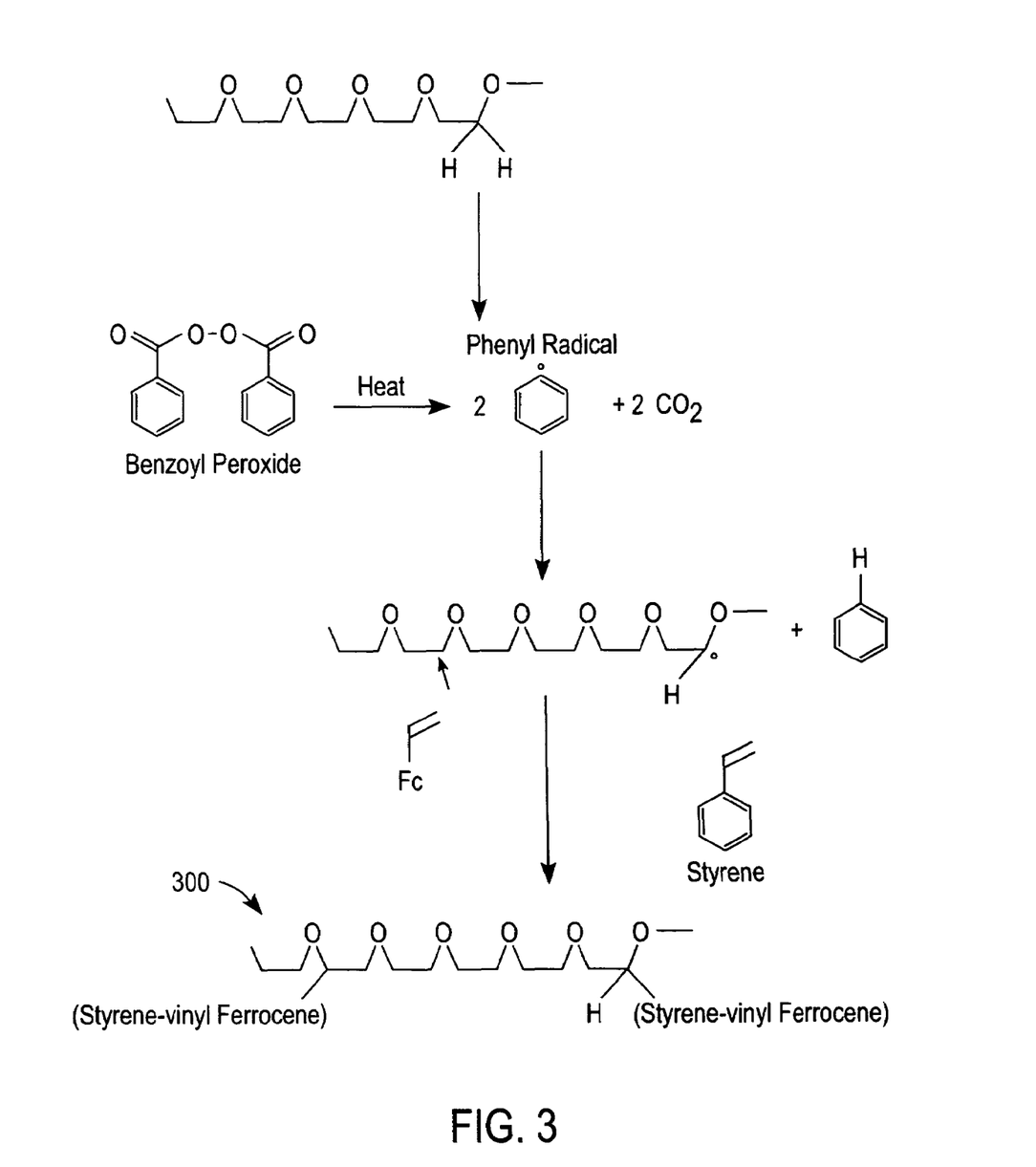
FIG. 3 is a simplified depiction of the grafting of VFc to polyethylene glycol (PEG) to form a redox polymer for use in electrochemical-based sensors according to exemplary embodiments of the present invention.

Redox polymers suitable for use in electrochemical-based sensors according to embodiments of the present invention can also be formed, for example, by grafting a hydrophilic polymer (e.g., polyethylene glycol (PEG), polyvinyl pyrrolidone or polyethyleneimine (PEI)) to a redox mediator. FIG. 3 depicts a reaction sequence for grafting VFc to PEG to form a redox polymer 300 for use in electrochemical-based sensors according to exemplary embodiments of the present invention. The reaction sequence depicted in FIG. 3 employs benzoyl peroxide as an initiator in the presence of styrene to form redox polymer 300 via a hydrogen abstraction mechanism.

Figure 4:
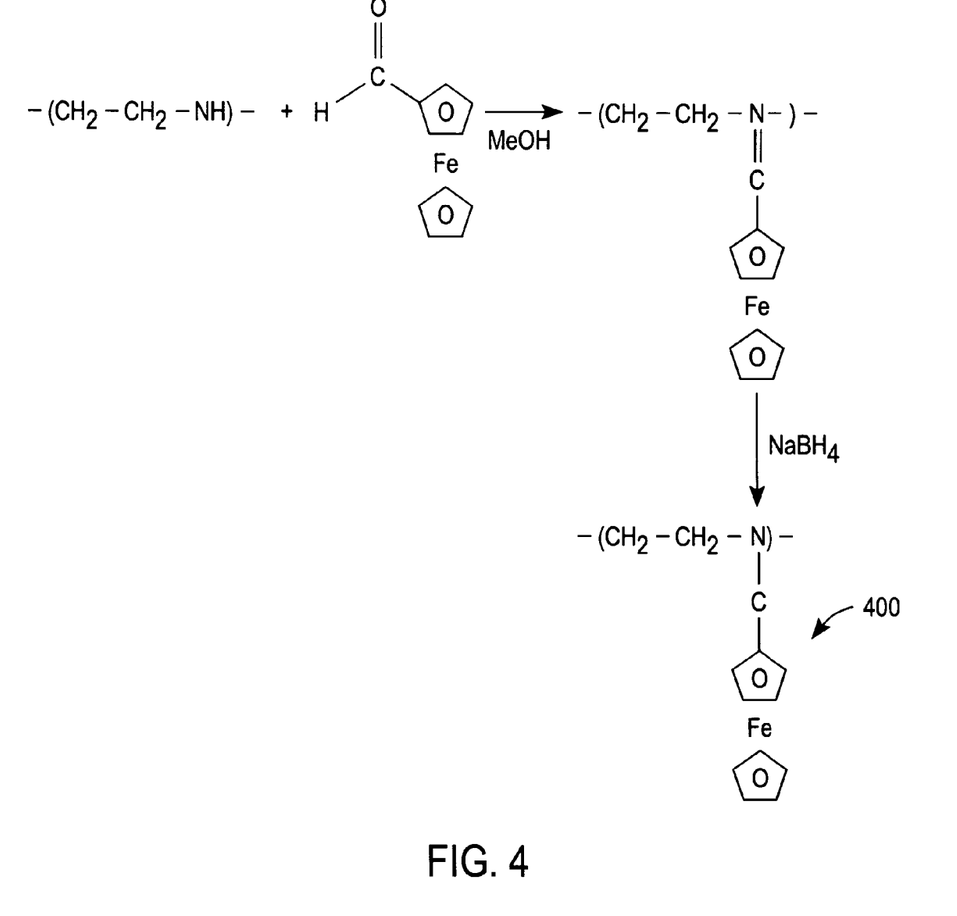
FIG. 4 is a simplified depiction of a reaction sequence for grafting ferrocene carboxaldehyde to polyethyleneimine (PEI)

FIG. 4 depicts a reaction sequence for grafting PEI to ferrocene carboxaldehyde to form a redox polymer 400 that is suitable for use in embodiments of electrochemical-based sensors according to the present invention. In the reaction sequence of FIG. 4, the secondary amine group of PEI forms a Schiff base (i.e., an imine) with the aldehyde group of the ferrocene carbvoxaldehyde. Since the Schiff base bond formation is unstable, sodium borohydride ($NaBH_4$) is used to reduce the imine to a tertiary amine.

The following examples illustrate and demonstrate further aspects and benefits of electrochemical-based sensors according to embodiments of the present invention.

EXAMPLE 1

Figure 5:
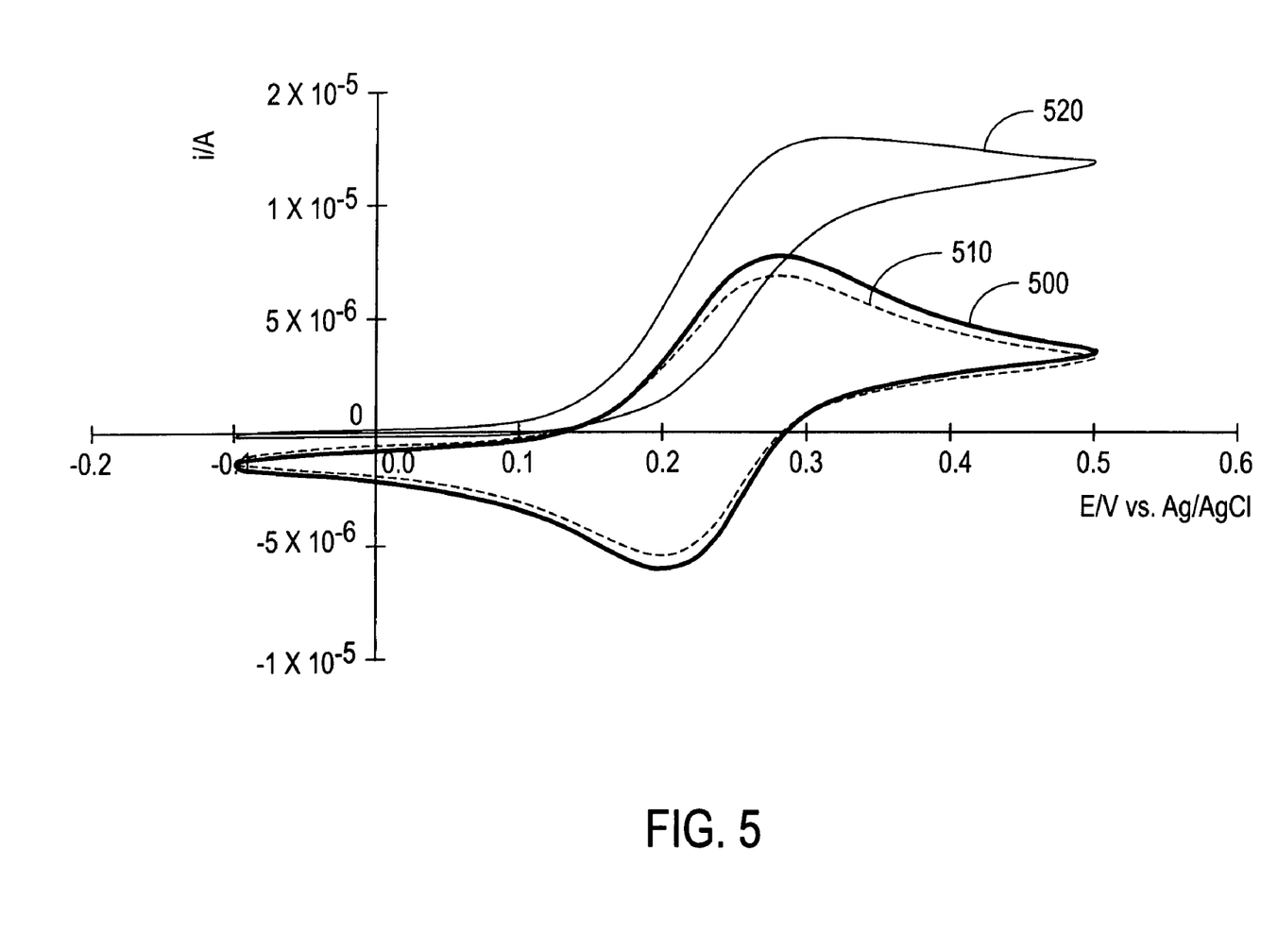
FIG. 5 is a cyclic voltammogram of an electrode tested in various solutions containing the redox polymer of FIG. 2.

Cyclic voltammetry (CV) with a 5% solution (in phosphate buffer saline (PBS)) of redox polymer 200 of FIG. 2 was performed with a glassy carbon electrode (GCE) at 50 mV/s between −0.1 and 0.5 V vs Ag/AgCl. Curve 500 of FIG. 5 was thereby obtained and demonstrates that redox polymer 200 is redox active at the glassy carbon electrode.

Next, glucose oxidase (a redox enzyme) was added to the PBS to a concentration of 0.05 wt %. The redox peaks of a subsequent CV scan decreased slightly, as shown by a curve 510 of FIG. 5. The small decrease in the oxidation and reduction peaks of curve 510 in comparison to curve 500 can be attributed to a small dilution resulting from the addition of glucose oxidase and/or an adsorption of glucose oxidase that resulted in the passivation of a small portion of the GCE.

Subsequently, glucose was added to the PBS to a concentration of 100 mM. This addition caused the oxidation current to increase, as demonstrated by CV curve 520 of FIG. 5. Since the glucose oxidase converted all of the ferricenium moieties at the electrode surface to ferrocene moieties, there was no reduction wave observed within curve 520. The characteristic shape of curve 520 may also be referred to as a catalytic wave in which the maximum current is proportional to the glucose concentration.

EXAMPLE 2

Figure 6:
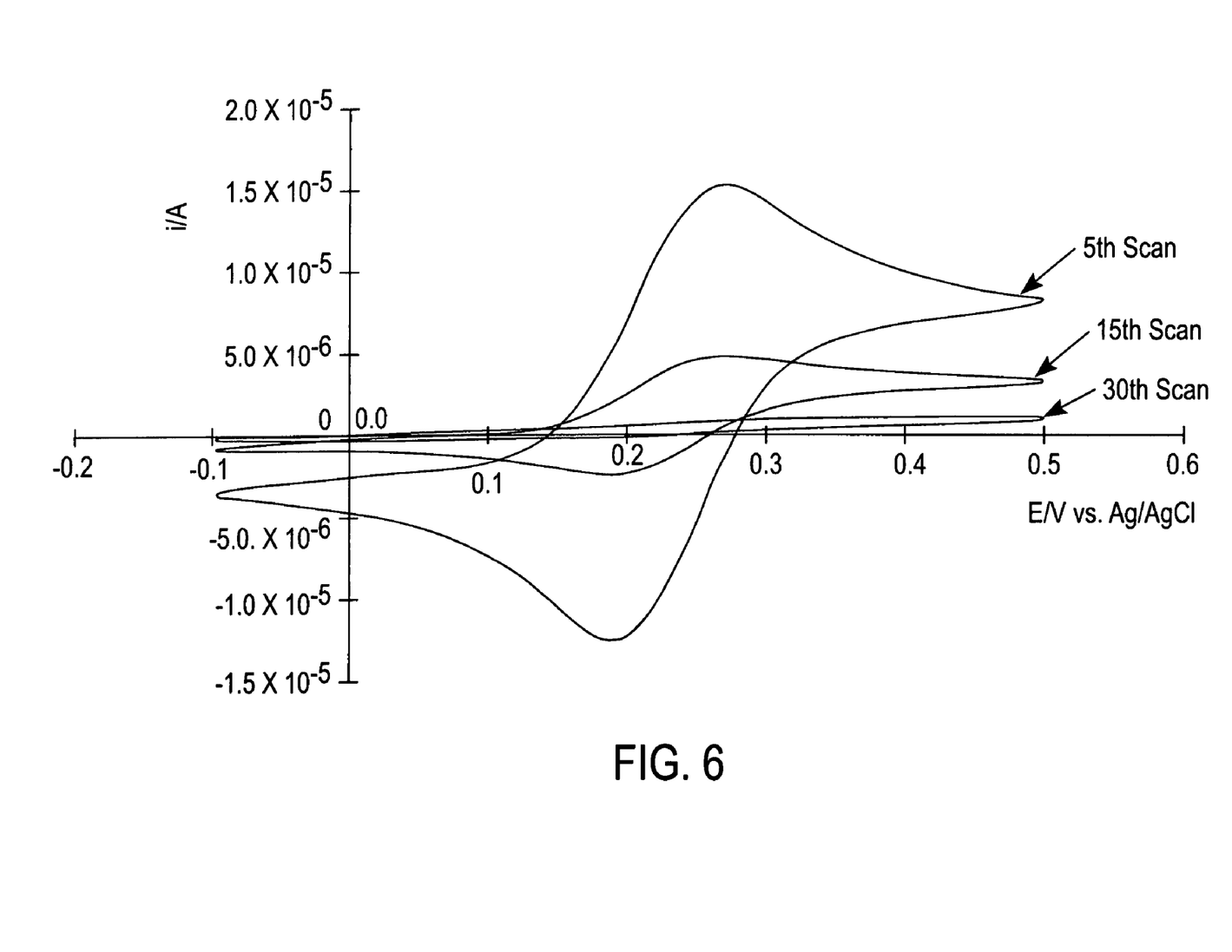
FIG. 6 is a cyclic voltammogram obtained for an electrode coated with the redox polymer of FIG. 2 in the absence of a dialysis membrane.

A GCE was dipped into a solution containing a 5% solution of redox polymer 200 of FIG. 2 dissolved in 2-isopropanol. The GCE was then removed from the 5% solution and allowed to dry. The GCE was subsequently immersed in PBS and tested using CV at 20 mV/s between −0.1 and 0.5 V vs. Ag/AgCl. The magnitude of the redox peaks decreased rapidly upon successive CV scans, as shown in FIG. 6. This indicates that redox polymer 200 washed off the GCE in the absence of a dialysis membrane to entrap redox polymer 200 in the vicinity of the GCE.

EXAMPLE 3

A coated electrode was prepared by applying 0.5 μL of a 5% (w/v) solution of redox polymer 200 dissolved in 2-isopropanol onto a carbon electrode (2.25 mm×2.25 mm) followed by drying in an oven at 50° C. for about 5 minutes. A dialysis membrane was then formed on the coated electrode by preparing a solution containing 2% (w/v) cellulose acetate (CA) and 0.7% PEG in acetone.

Figure 7:
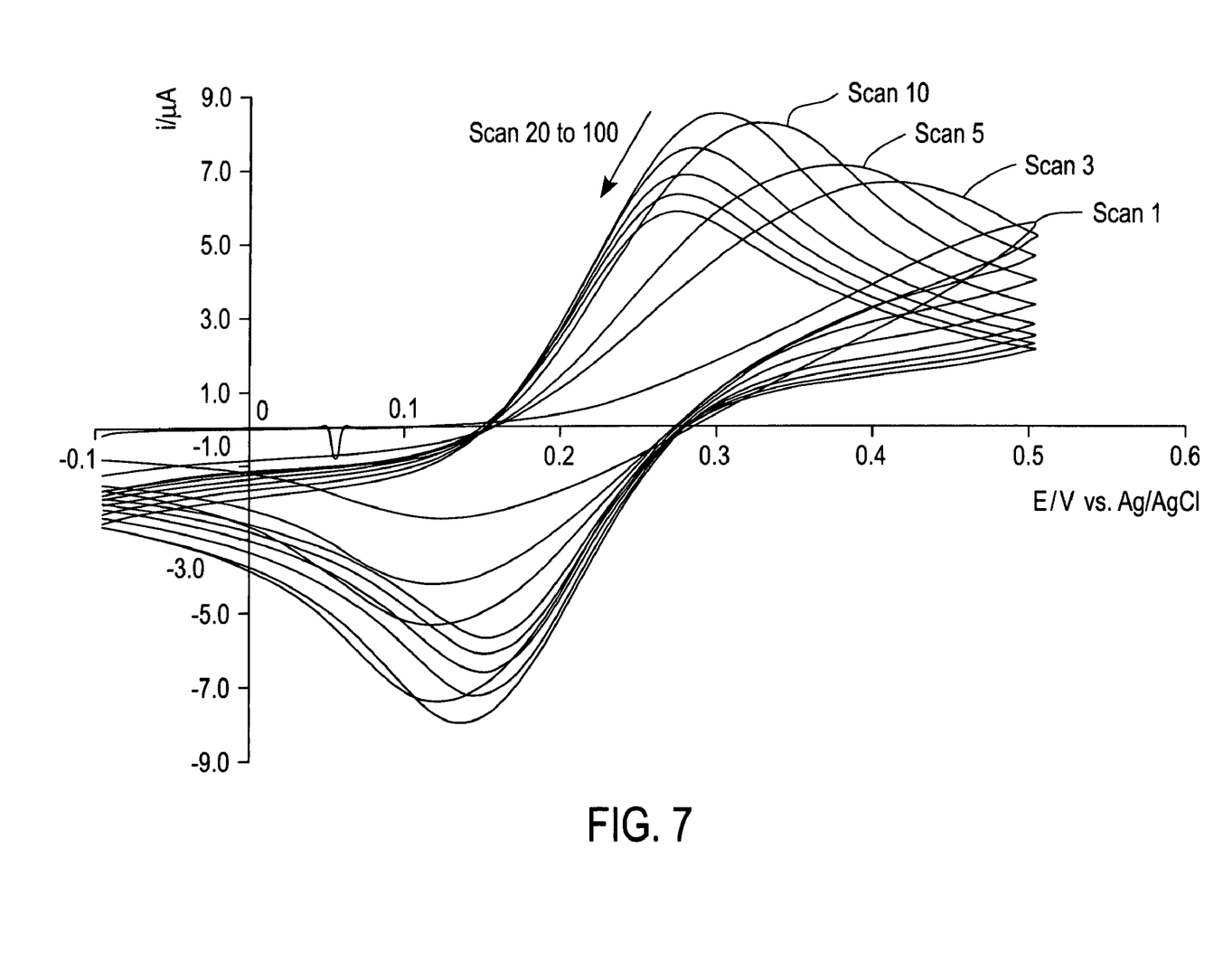
FIG. 7 is a cyclic voltammogram obtained for an electrode coated with the redox polymer of FIG. 2 and then subsequently coated with a dialysis membrane.

Next, 0.8 μL of the CA/PEG mixture was applied to the coated electrode and dried in the oven at 50° C. for 30 minutes. The CA/PEG mixture formed a cast dialysis membrane that retained large molecular weight redox polymer 200 in the vicinity of the carbon electrode. The GCE prepared as described immediately above was immersed in PBS and tested by CV at 20 mV/s between −0.1 and 0.5 V vs. Ag/AgCl. The magnitude of the redox peaks initially increased upon successive CV scans due of an initial wetting of the electrode and then gradually decreased, as shown in FIG. 7. It should be noted that the observed rate of decrease in FIG. 7 is less than the rate observed in FIG. 6. This indicates that the dialysis membrane of this example aided in the entrapment of redox polymer 200 in the vicinity of the carbon electrode.

EXAMPLE 4

An electrochemical-based glucose sensor without a dialysis membrane was prepared by applying 0.5 µL of a 5% (w/v) solution of redox polymer 200 onto a carbon electrode (2.25 mm×2.25 mm) followed by drying in an oven at 50° C. for about 5 minutes. Next, 1 µL of a 10% (w/v) glucose oxidase solution in PBS was applied to the electrode and then dried in the oven at 50° C. for 10 minutes.

EXAMPLE 5

An electrochemical-based glucose sensor was prepared in a manner similar to that of Example 4, except that the electrochemical-based glucose sensor included a dialysis membrane coated thereon. More specifically, the dialysis membrane coated thereon was a cast polymer membrane prepared from a solution containing 2% (w/v) CA and 0.7% PEG in acetone. The dialysis membrane was formed by applying 0.8 µL of this CA/PEG mixture to an electrochemical-based glucose sensor as described in Example 4 and then drying the sensor in the oven at 50° C. for 30 minutes. The CA and PEG solution formed a cast dialysis membrane that retains large molecular weight redox polymer 200 and the redox enzyme (i.e., glucose oxidase) whilst allowing small molecular weight analytes, such as glucose, to pass therethrough.

EXAMPLE 6

The electrochemical-based glucose sensor of Example 4 (without a dialysis membrane) and the electrochemical-based glucose sensor of Example 5 (with a dialysis membrane) were independently tested in the presence of 100 mM glucose. The working electrodes of each electrochemical-based sensor were scanned between −0.1 and 0.5 V vs. Ag/AgCl at a rate of 20 mV/s while open to the atmosphere and at room temperature. The resulting catalytic waves were recorded every 10 minutes over a 100 minute time interval.

Figure 8A:
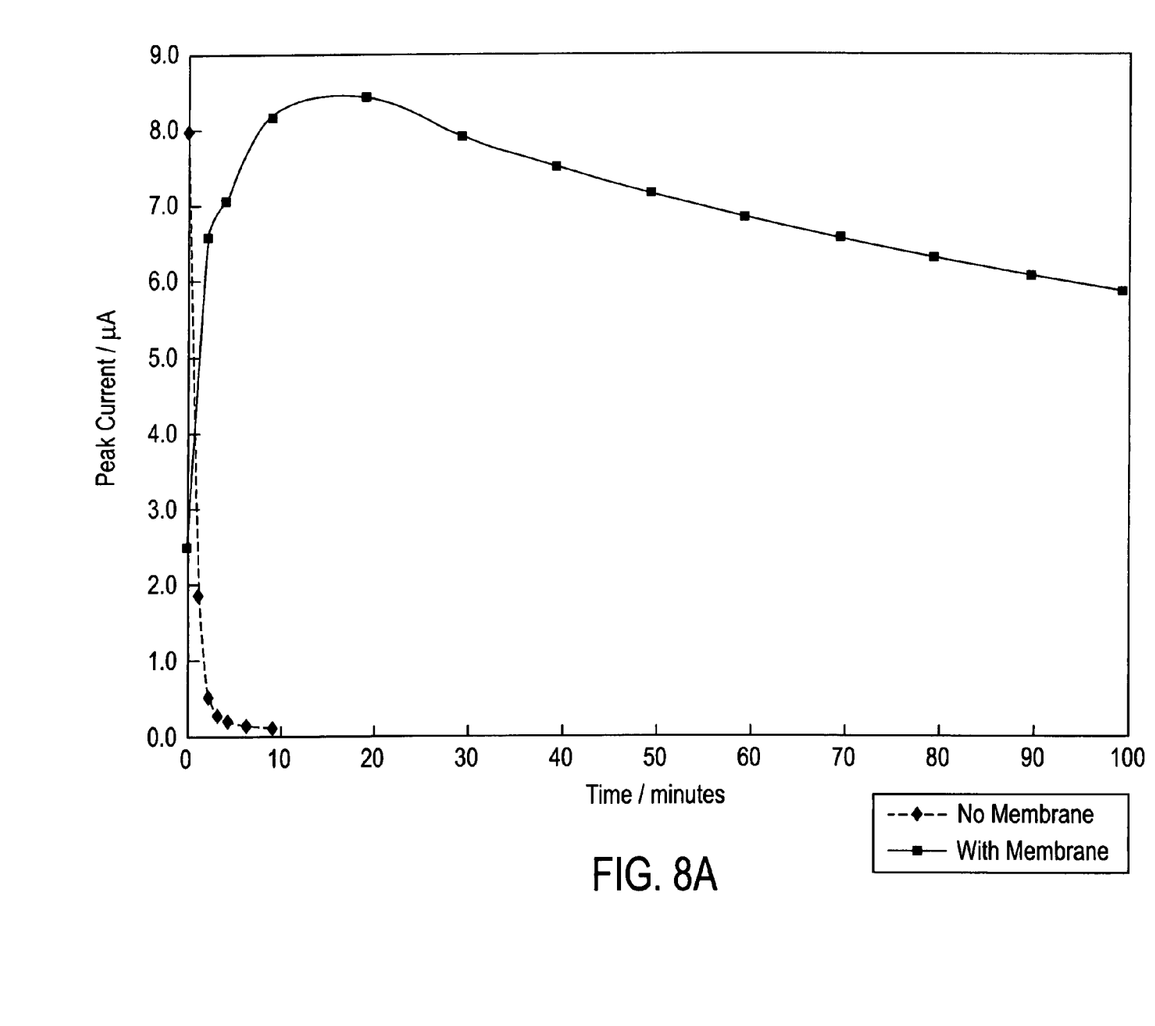
Figure 8B:
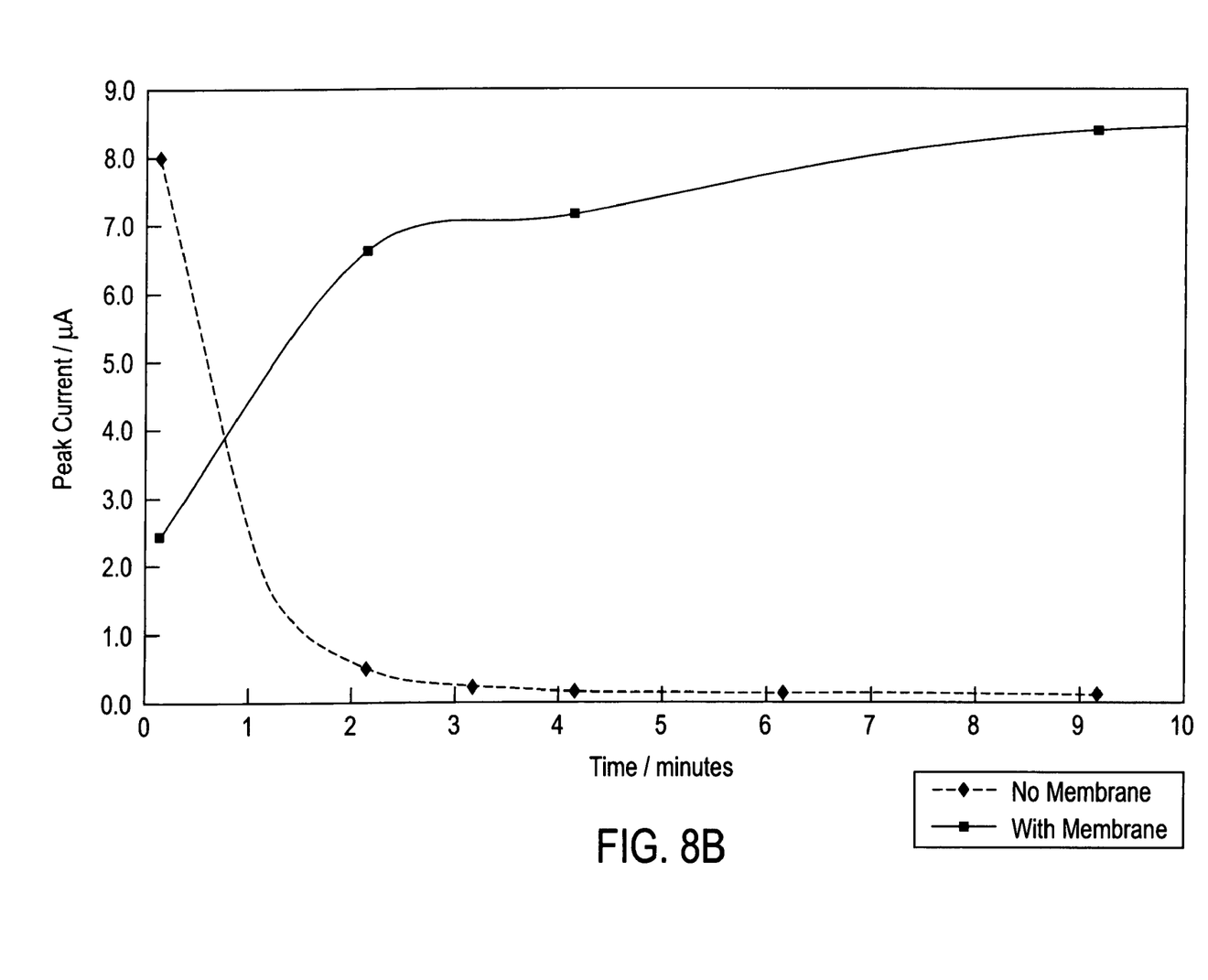

FIGS. 8A and 8B depict that the catalytic waves exhibited an oxidation current that decreased rapidly for the electrochemical-based glucose sensor that did not have a dialysis membrane. This suggests that redox polymer 200 washed off the electrode of such an electrochemical-based glucose sensor. However, for the electrochemical-based glucose sensor that included a dialysis membrane, the catalytic wave exhibited an oxidation current which decreased more slowly, thus indicating that the redox mediator and redox enzyme were retained in the vicinity of the electrode by the dialysis membrane.

EXAMPLE 7

An electrochemical-based glucose sensor with a dialysis membrane was prepared in a manner similar to that of Example 5, except that the dialysis membrane was a cross-linked polymer film that included PEI and PPGDGE. To form such a dialysis membrane, 52 mg of PEI and 106 mg of PPGDGE were mixed together to form a PEI/PPGDGE mixture in 1 mL of 2-isopropanol. Next, 0.8 µL of the PEI/PPGDGE mixture was applied to a coated carbon electrode (prepared as in Example 4 above) and dried in an oven at 50° C. for 30 minutes. The PEI and PPGDGE solution formed a dialysis membrane in the form of a cross-linked polymer dialysis membrane that retains large molecular weight redox polymer 200 and the redox enzyme whilst allowing small molecular weight analytes, such as glucose, to penetrate therethrough.

It is contemplated without being bound that the hydrophilic nature of the cross-linked polymer dialysis membrane, formed from the PEI and PPGDGE solution, results in membrane swelling when in contact with an aqueous solution. This swelling provides the cross-linked polymer dialysis membrane with hydrogel characteristics. Therefore, the resulting membrane can be referred to as a hydrogel layer. Furthermore, the penetration of relatively low molecular weight analytes (e.g., glucose) through such a hydrogel layer is much faster than the penetration of relatively high molecular weight redox polymers and redox enzymes.

EXAMPLE 8

A redox polymer suitable for use in electrochemical-based sensors according to the present invention was synthesized by a free radical co-polymerization using 10.4 g of NVP, 0.87 g of vinylferrocene (VFc), and 0.11 g of 2,2'-azobisisobutyronitrile (AIBN) (see the sequence depicted in FIG. 2). The reaction was performed in a round bottom flask. Before initiating the reaction, the reaction solution was deoxygenated by bubbling nitrogen therethrough for one hour. The reaction flask was then heated to 70° C. in an oil bath for 24 hours with continuous magnetic agitation under a nitrogen atmosphere.

The resulting redox polymer was dissolved in dichloromethane and precipitated out of solution with diethyl ether. Next, the precipitated redox polymer was filtered and dried in an oven at 50° C. Low molecular weight portions of the redox polymer were then eliminated through dialysis against deionized water. The dialysis tubing was a cellulose membrane with a molecular cutoff of 16 Kg/mol.

EXAMPLE 9

A redox polymer suitable for use in electrochemical-based sensors according to embodiments of the present invention was synthesized by a grafting process (as depicted in FIG. 3). A VFc solution was first prepared by dissolving 0.6 g of VFc in 2.1 g of styrene. In a separate container, a benzoyl peroxide suspension was prepared by suspending 0.24 g of benzoyl peroxide (70%) in 1.37 g xylene. In yet another separate container, a PEG solution was prepared by mixing 10 g of PEG (molecular weight 8 Kg/mol) with 20 g of ethoxyethanol and then warmed to 90° C.

Next, the VFc solution was added to the PEG solution at 90°C. to form a VFc/PEG mixture. Immediately after the addition of the VFc solution, the benzoyl peroxide suspension was added to the VFc/PEG mixture to form a reaction mixture. Upon initiation of grafting, the reaction mixture formed into single phase that was red-orange in colour. The reaction mixture was stirred at 90° C. for 2 hours and then allowed to continue stirring overnight at 70° C. The reaction mixture was, thereafter, transferred to 50 ml of analar water, causing a red/brown emulsion to be formed that contained a redox polymer. The red/brown emulsion was suitable for use in coating a GCE during the preparation of electrochemical-based glucose sensor according to an embodiment of the present invention.

EXAMPLE 10

Yet another redox polymer suitable for use in electrochemical-based sensors according to embodiments of the present invention was synthesized by a grafting process (as depicted in FIG. 4). In this synthesis, 0.3 g of ferrocene carboxaldehyde was mixed with 50 ml of dry methanol and 18 g of PEI to form a reaction solution. The number average molecular weight (Mn) of the PEI was 10 Kg/mol and the weight average molecular weight (Mw) was 25 Kg/mol.

The reaction solution was subsequently stirred at ambient for 2 hours. The reaction was monitored by removing aliquots of the reaction solution and performing thin layer chromatography (TLC) with a methanol elutant. The results of TLC testing indicated that all of the ferrocene carboxaldehyde had reacted to an imine after 2 hours.

Next, 100 mg of sodium borohydride was added to 10 ml of methanol, which was then added to the reaction solution to reduce the imine to a tertiary amine. After adding the sodium borohydride, the reaction solution was stirred for an additional 2 hours, followed by the gradual addition of 15 ml of water. Next, a further 20 ml of water was quickly added to insure that all of the sodium borohydride had reacted. The reaction solution was then extracted with 100 ml of diethyl ether to remove any possible organic impurities. The organic phase was then discarded. After the extraction step, the reaction solution was dried overnight in an oven at 70° C. to yield a redox polymer suitable for use in embodiments of electrochemical-based sensors according to the present invention.

It should be understood that various alternatives to the embodiments of the invention described herein may be employed in practicing the invention. It is intended that the following claims define the scope of the invention and that structures within the scope of these claims and their equivalents be covered thereby.

What is claimed is:

1. An electrochemical-based sensor comprising:
    an electrode with at least one electrode surface;
    a film disposed on the electrode surface, the film including:
        a redox enzyme; and
        a hydrophilic redox polymer; and
    a dialysis membrane disposed on the film,
    wherein the dialysis membrane serves to entrap the redox enzyme and hydrophilic redox polymer in the vicinity of the electrode; and
    wherein the redox enzyme and hydrophilic redox polymer are of a molecular weight that essentially precludes passage of the redox enzyme and hydrophilic redox polymer through the dialysis membrane, thus entrapping the redox enzyme and hydrophilic redox polymer in the vicinity of the electrode;
    wherein the redox polymer is synthesized by co-polymerizing N-vinylpyrrolidinone and vinylferrocene.

2. The electrochemical-based sensor of claim 1 further including a working electrode.

3. An electrochemical-based sensor comprising:
    an electrode with at least one electrode surface;
    a film disposed on the electrode surface, the film including:
        a redox enzyme; and
        a hydrophilic redox polymer; and
    a dialysis membrane disposed on the film,
    wherein the dialysis membrane serves to entrap the redox enzyme and hydrophilic redox polymer in the vicinity of the electrode; and
    wherein the redox enzyme and hydrophilic redox polymer are of a molecular weight that essentially precludes passage of the redox enzyme and hydrophilic redox polymer through the dialysis membrane, thus entrapping the redox enzyme and hydrophilic redox polymer in the vicinity of the electrode;
    wherein the redox polymer is synthesized by grafting vinylferrocene to polyethylene glycol.

4. An electrochemical-based sensor comprising:
    an electrode with at least one electrode surface;
    a film disposed on the electrode surface, the film including:
        a redox enzyme; and
        a hydrophilic redox polymer; and
    a dialysis membrane disposed on the film,
    wherein the dialysis membrane serves to entrap the redox enzyme and hydrophilic redox polymer in the vicinity of the electrode; and
    wherein the redox enzyme and hydrophilic redox polymer are of a molecular weight that essentially precludes passage of the redox enzyme and hydrophilic redox polymer through the dialysis membrane, thus entrapping the redox enzyme and hydrophilic redox polymer in the vicinity of the electrode;
    wherein the redox polymer is synthesized by grafting ferrocene carboxaldehyde to polyethyleneimine (PEI).

* * * * *

UNITED STATES PATENT AND TRADEMARK OFFICE
CERTIFICATE OF CORRECTION

PATENT NO. : 7,572,356 B2  Page 1 of 1
APPLICATION NO. : 10/931724
DATED : August 11, 2009
INVENTOR(S) : Rodgers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1304 days.

Signed and Sealed this

Fourteenth Day of December, 2010

David J. Kappos
*Director of the United States Patent and Trademark Office*